US009494536B1

(12) United States Patent
Barney et al.

(10) Patent No.: US 9,494,536 B1
(45) Date of Patent: Nov. 15, 2016

(54) METHODS FOR PREDICTING CORROSION RATE OF CRUDE OIL DERIVED SAMPLES USING X-RAY ABSORPTION SPECTROSCOPY

(71) Applicants: Monica Michele Barney, San Francisco, CA (US); Andrew B. Nissan, Richmond, CA (US); Graham N. George, Saskatoon (CA)

(72) Inventors: Monica Michele Barney, San Francisco, CA (US); Andrew B. Nissan, Richmond, CA (US); Graham N. George, Saskatoon (CA)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 14/727,395

(22) Filed: Jun. 1, 2015

(51) Int. Cl.
*G01N 23/223* (2006.01)
*G01N 23/207* (2006.01)

(52) U.S. Cl.
CPC ........ *G01N 23/2076* (2013.01); *G01N 23/223* (2013.01)

(58) Field of Classification Search
None
See application file for complete search history.

(56) References Cited

U.S. PATENT DOCUMENTS

| 5,744,702 A * | 4/1998 | Roussis | G01N 33/287 |
| | | | 73/53.01 |
| 2013/0289320 A1* | 10/2013 | Barney | C10G 75/00 |
| | | | 585/3 |

FOREIGN PATENT DOCUMENTS

| WO | 9958951 | 11/1999 |
| WO | 2004111624 | 11/2004 |
| WO | 2014151460 | 9/2014 |

OTHER PUBLICATIONS

McConomy, H.F., High Temperature Sulfidic Corrosion in Hydrogen-Free Environments, API Proceedings 1963, 43 (III), 78.
Foroulis, Z.A., High temperature degradation of structure materials in environments encountered in the petroleum and petrochemical industries: Some mechanistic observations. *Anti-Corrosion Methods and Materials* 1985, 32(11), 4.
Pomerantz, A.E., et al., Sulfur speciation in kerogen and bitumen from gas and oil shales. Organic Geochemistry 2014, 68, 5.
Strel'nikova, E.B., Goncharov, I.V., and Serebrennikova, O.V. Concentration and Distribution of Oxygen-Containing Compounds in Crude Oils from the Southeastern Part of Western Siberia. Petroleum Chemistry 2012, 52(4), 278-283.

(Continued)

*Primary Examiner* — Michael Logie
(74) *Attorney, Agent, or Firm* — Karen R. DiDomenicis

(57) ABSTRACT

A method for predicting the corrosion rate of crude oil or other related process streams is provided. The method includes using x-ray absorption spectroscopy to characterize heteroatom species present by functional group and quantify the relative amount of each species in a plurality of samples. The corrosion rate of each sample is measured. A correlation between the relative amount of each species and the corrosion rate is determined and used to create a corrosion prediction model. The corrosion prediction model can be used so that corrosion rate can be predicted for a sample solely from the spectroscopy measurement of the relative amounts of each relevant species.

9 Claims, 5 Drawing Sheets

(56) References Cited

OTHER PUBLICATIONS

ASTM D3227-04a (2010). "Standard Test Method for (Thiol Mercaptan) Sulfur in Gasoline, Kerosene, Aviation Turbine, and Distillate Fuels (Potentiometric Method)" ASTM International, West Conshohocken, PA, 2004, DOI: 10.1520/D3227-04R10, www.astm.org.
George, G. N., George, S. J. & Pickering, I. J. (2001). EXAFSPAK, http://ssrl.slac.stanford.edu/exafspak.htm.
API Recommended Practice 939-C, "Guidelines for Avoiding Sulfidation (Sulfidic) Corrosion Failures in Oil refineries", (Washington, D.C.: API).
Gutzeit, J., "High temperature sulfidic corrosion of steels", in Process Industry Corrosion—The Theory and Practice. National Association of Corrosion Engineers 1986.
George, G.N., Gorbaty, M.L. and Kelemen, S.R., Sulfur K-edge x-ray absorption spectroscopy of petroleum asphaltenes and model compounds. *J. Am. Chem. Soc.* 1998, 111, 3182.

\* cited by examiner

METHODS FOR PREDICTING CORROSION RATE OF CRUDE OIL DERIVED SAMPLES USING X-RAY ABSORPTION SPECTROSCOPY

TECHNICAL FIELD

The present disclosure relates to methods and systems for predicting a corrosion rate for crude oil derived samples using X-ray absorption spectroscopy to identify potentially corrosive functional groups in the samples and a model correlating corrosion rate and x-ray absorption fine structure data.

BACKGROUND

The ability to predict how corrosive a crude oil or its distilled fractions will be during high temperature processing in contact with steel and other materials of containment would be highly useful to those involved in the extracting, processing and refining of petroleum. With such corrosivity information, refiners would have a more accurate understanding of the risks involved in processing a proposed crude or its distillates. For example, if a crude oil contains a high level of corrosive species, special care could be taken in processing it, while a crude oil containing fewer corrosive species could be processed confidently with standard safeguards in place. Other strategies could be employed such as blending the oil with different crudes to reduce the concentration of corrosive species. Thus, having the ability to predict corrosivity would reduce risk levels and enable smarter strategies in processing a variety of crude oils.

One element found in crude oils and known to cause corrosion is sulfur. An industry standard for predicting the rates of sulfidation, known as the "modified McConomy curves," shows corrosion rate of various alloys as a function of temperature using empirical data of crudes with 0.6 wt. % sulfur. To account for varying concentrations, a correction factor for increasing sulfur content is included. While the total amount of sulfur in crude can be measured quite easily, this value is not a very accurate indicator of how corrosive a crude oil will be when it is processed at elevated temperature. This lack of correlation stems from the large range of reactivity that exists between various types of organic sulfur compounds found in petroleum and metals. These differences are apparent in high temperature tests of steel coupons exposed to gaseous streams of individual sulfur compounds containing the functional groups found in crude, with disulfides showing at least an order of magnitude greater sulfidation rate than thiophenes. Ranking of corrosivity by sulfur compound types has been done for idealized lab samples, but not for real crude oil samples because of the inability to measure how much of sulfur compound type is in the oil.

There exists a need for a method which would identify corrosive species and relative amounts of the corrosive species in crude oil and its distilled fractions to aid in predicting how corrosive a specific type of crude oil or distilled fraction is likely to be.

SUMMARY

In one aspect, a method is provided for predicting a corrosion rate of a crude oil derived sample. The method includes creating a corrosion prediction model. The corrosion prediction model is created by subjecting a plurality of samples to a range of x-ray energies, to obtain x-ray absorption fine structure data for each sample in the form of absorbance versus x-ray energy wherein the x-ray absorption fine structure data for each sample has an edge associated with a rise in absorbance as x-ray energy increases. Functional groups present in each of the plurality of samples are identified and quantified relative to one another from analysis of the x-ray absorption fine structure data. A corrosion rate for each of the plurality of samples is determined. The corrosion rate determined for each of the plurality of samples is correlated with the relative amounts of each functional group identified in each sample to create the corrosion prediction model.

Once the corrosion prediction model is created, the corrosion prediction model can be used to predict a corrosion rate of a crude oil derived sample for which the corrosion rate is not known. The crude oil derived sample is subjected to a range of x-ray energies to obtain x-ray absorption fine structure data in the form of absorbance versus x-ray energy wherein the x-ray absorption fine structure data for the crude oil derived sample has an edge associated with a rise in absorbance as x-ray energy increases. Functional groups present in the crude oil derived sample are identified and quantified relative to one another from analysis of the x-ray absorption fine structure data. The corrosion prediction model is then solved for corrosion rate as a function of the relative amounts of the functional groups identified in the crude oil derived sample to obtain a prediction of the corrosion rate of the crude oil derived sample.

In another aspect, a system is provided for predicting a corrosion rate of a crude oil derived sample. The system includes a source of x-ray energy capable of subjecting a sample in a sample holder to a range of x-ray energies. The system includes a processor for receiving x-ray absorption fine structure data for samples in the form of absorbance versus x-ray energy wherein the x-ray absorption fine structure data for each sample has an edge associated with a rise in absorbance as x-ray energy increases. The x-ray absorption fine structure data can be compared to a set of reference patterns for identifying and quantifying relative amounts of functional groups present in each sample. The system includes a corrosion rate determination means for determining a corrosion rate for each of the plurality of samples. The system includes a processor capable of receiving and correlating the corrosion rate for each sample and the relative amounts of each functional group identified in each sample to create a corrosion prediction model. The system includes memory connected to the processor for storing the corrosion prediction model. The system includes a processor connected to the memory for solving the corrosion prediction model for corrosion rate as a function of the relative amounts of the functional groups identified in the crude oil derived sample to obtain a prediction of the corrosion rate of the crude oil derived sample.

DESCRIPTION OF THE DRAWINGS

These and other objects, features and advantages of the present invention will become better understood with reference to the following description, appended claims and accompanying drawings where:

DETAILED DESCRIPTION OF THE PREFERRED EMBODIMENTS

Figure 1:
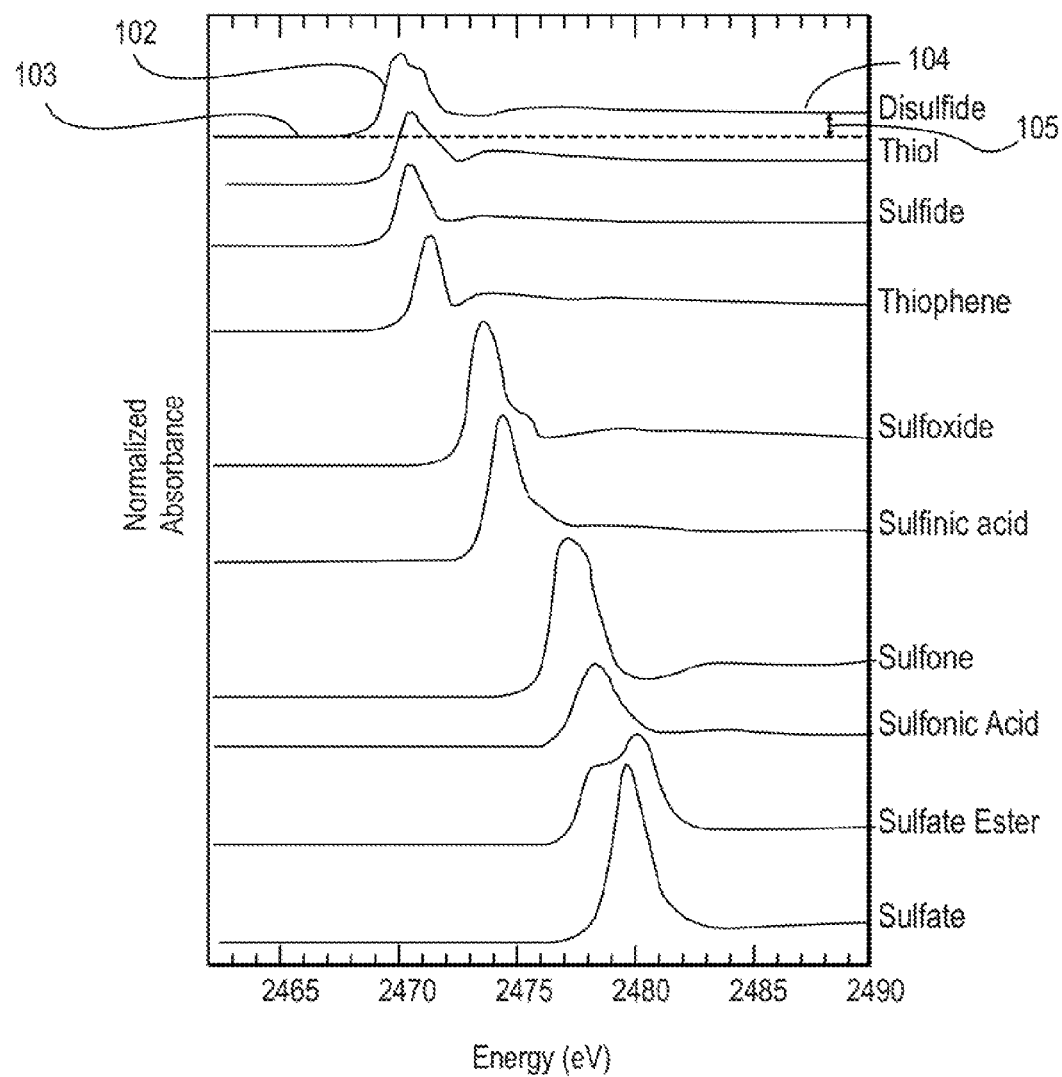
FIG. 1 is a graph of normalized intensity ratio ($I_o/I_f$) versus energy in eV showing the variation in energy of a range of sulfur compounds present.

The disclosure relates to a method for improving the corrosivity predictions of petroleum and its derivatives by using x-ray absorption spectroscopy (XAS) to identify the relative amounts of heteroatom components by functional group. The steps of the method include introducing a small volume of sample into a sample holder that will allow a consistently thin layer of sample to be held in the path of a tunable x-ray beam. By sample is meant a small volume of crude oil derived fluid or solid. The sample can be any sample selected from crude oil samples, distilled fractions of crude oil, residual oil, samples produced from the processing or extraction of crude oil, water samples produced with crude oil and combinations thereof. The sample can contain heteroatoms in a concentration ranging from a few millimolar or 100 ppm to about 2 wt %. The sample is subjected to scanning by the x-ray through a range of energies relevant to the element or functional group of interest while collecting signal from ion chambers positioned upstream and downstream of the sample. X-rays are generated in such a way as to be monochromatic and tunable such that a range of energies is provided to collect a full x-ray absorption pattern. A monochromater can be used to transform a "white," full-spectrum x-ray beam to a single energy (monochromatic) beam. In one embodiment, this can be over a range of from 30 to 100 eV. This can accomplished with a lab scale unit or with the use of a high brightness x-ray synchrotron. The signal collected is absorption spectra for each type of element or functional group of interest contained in the sample. The transmitted, fluorescence, or transmitted and fluorescence x-ray signals can be collected.

The collected spectra are normalized. The normalized spectra are compared to those of known standard spectra also referred to as reference patterns to determine what combination of and relative amounts of species are in the sample. The method of pattern matching to determine what combination of and relative amounts of species are in the sample is also referred to as peak deconvolution.

The corrosion rate of the sample is measured while the sample is exposed to metal at high temperature. The experimentally obtained corrosion rate of the sample is compared to the relative amounts of each species identified in the sample. In one embodiment, a sample is introduced into an autoclave along with a coupon of the metal alloy of interest. The metal coupon can be in any size or shape for weight loss (mils/year) measurements. In such case, a coupon of the alloy is weighed and measured before and after the autoclave test and a weight loss and corrosion rate is calculated. Alternatively, the sample and the alloy of interest can be contained in a probe that measures real time corrosion rate via the change in the resistance across the anode. The autoclave can be capable of maintaining a temperature of up to 750° F. and pressure of 1000 psi. A coupon of the alloy of interest can be inserted into the crude oil derived sample and the autoclave then sealed. The test temperature is applied while the oil is agitated. The metal is exposed to these conditions for a period of time, typically between 8 hours and 6 months. A range of temperatures can be tested. In one embodiment, a temperature range of from 450 to 750° F. is tested to cover the ranges applicable to sulfidation from sulfur species and organic acid corrosion from oxygen species.

A plurality of samples, for example, at least 5 samples, is thus processed, both by x-ray absorption spectroscopy (XAS) to identify the relative amounts of heteroatom components by functional group, and by measuring corrosion rate. A database of XAS data and corrosion rate data is thus collected.

The corrosion rates of all of the samples are compared to the relative amounts of each species identified in all of the samples, respectively, to develop a correlation. The correlation is in the form of a model or a mathematical equation relating corrosion rate to the amounts of various species in a sample. The model of the correlation using can be developed standard methods such as multiple regression. The correlation or model can be used to predict corrosion rates of crude oils and crude oil derived samples solely from XAS data and species identification.

In order to fully speciate heteroatom compounds in oil by functional group, the present method is chemically selective, i.e., capable of separating and detecting compounds containing the specific element of interest. Elements of interest can include sulfur, nitrogen, oxygen, chlorine for example. The method is capable of determining the presence of elements and functional groups of interest at ppm levels. The method is chemically selective because the electronic transitions that cause the measured signal occur at element specific energies, with the higher the atomic number of the element, the higher the energy. The energy of the primary absorption edge, also referred to herein as the edge or the white line, varies around this element specific value by oxidation state. The most reduced forms show an edge at lower energy and more oxidized forms at higher energy. As an example, spectra of various sulfur compounds are shown in FIG. 1. FIG. 1 is a set of graphs of x-ray absorption fine structure data. Each graph is a plot of normalized intensity ratio ($I_o/I_f$) also referred to as normalized absorbance versus energy in eV. FIG. 1 shows the variation in energy for a range of sulfur compounds (disulfide, thiol, sulfide, and so on through sulfate). The x-ray absorption fine structure data for each sample has an edge 102 associated with a rise in absorbance as x-ray energy increases. The difference between the pre-edge 103 and the post-edge 104 levels on the graph is referred to as the edge jump 105.

XAS is not limited by viscosity or boiling point. With consistent sample preparation, it can also be applied to solids. Once the data is normalized, the peak height of the edge from each component correlates with its fraction so the relative amount of each species can be identified. This is possible because the overall absorption intensity is a linear combination of each individual component and the separate contributions from each component can be deconvoluted to yield the relative amounts of each one. As would be understood by one of skill in the art, in one embodiment, the x-ray absorption fine structure data can be normalized by rescaling the data so that the edge jump is 1.0, meaning the edge jump has an ordinate magnitude of 1.0. By "ordinate magnitude" is meant magnitude on the ordinate scale (i.e., the normalized intensity ratio scale in the case of normalized intensity ratio versus energy).

In one embodiment, part of the XAS spectra, called the X-ray Absorption Near Edge Spectroscopy (XANES), is used to provide chemical information about the nature and amounts of the heteroatom species present in a sample of crude oil or its derived distillate fractions.

Figure 3:
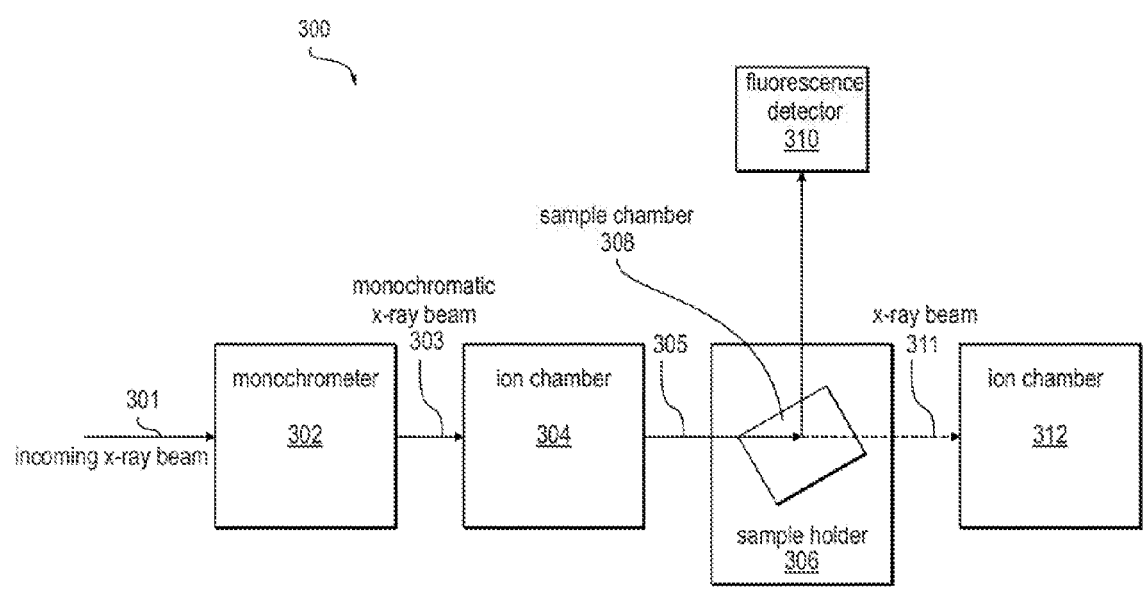
FIG. 3 is a schematic diagram illustrating an experimental setup according to one exemplary embodiment

In one embodiment, an experimental setup 300 such as that shown in FIG. 3 is used. An incoming x-ray beam 301 can be passed through a monochrometer 302 in order to filter the x-ray beam to a single energy, monochromatic x-ray beam 303. The monochromatic x-ray beam 303 passes through an ion chamber 304 for collecting an incoming x-ray intensity signal $I_o$. The x-ray beam leaves the ion chamber 304 as 305 and impinges on the sample holder 308 within the sample chamber 306. The sample holder 308 is positioned at a 45° angle with respect to x-ray beam 305. A fluorescence detector 310 is positioned to measure a fluorescence intensity signal $I_f$. In the case of a sample which is sufficiently thin, transmitted x-ray beam 311 can be measured in ion chamber 312 to measure transmitted x-ray intensity $I_2$.

Figure 4:
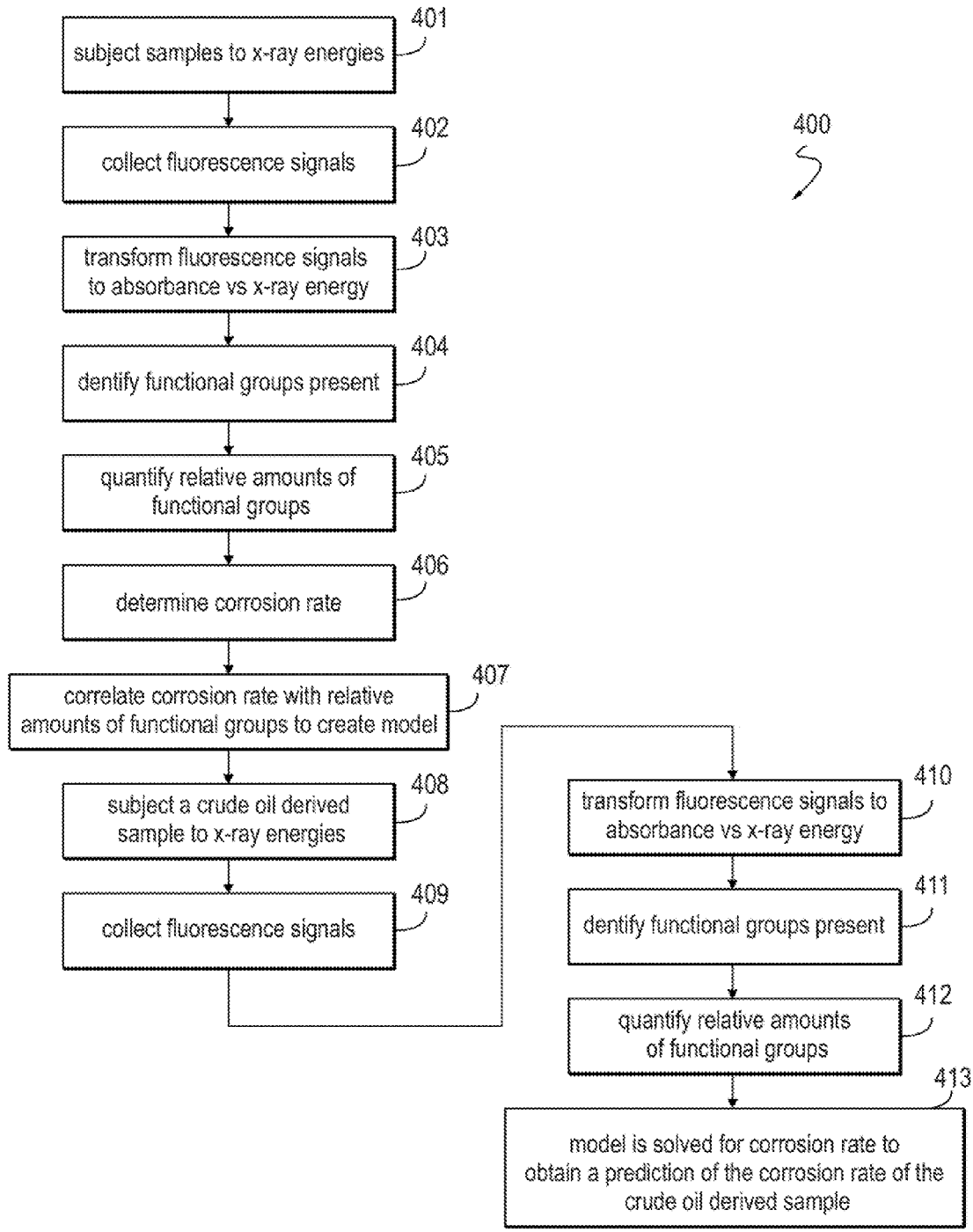
FIG. 4 is a flowchart illustrating the steps of the method according to one exemplary embodiment.

A flowchart of the steps of a method 400 for predicting a corrosion rate of a crude oil derived sample in one embodiment is illustrated in FIG. 4. In steps 401 through 407, a corrosion prediction model is created. In step 401, a plurality of samples is subjected to a range of x-ray energies. In step 402, transmitted x-ray intensity or fluorescence signals are collected from the plurality of samples. In 403, the collected transmitted x-ray intensity or fluorescence signals is transformed to x-ray absorption fine structure data for each sample in the form of absorbance versus x-ray energy. In 404, the functional groups present in each of the plurality of samples are identified from the x-ray absorption fine structure data. In 405, the relative amounts of the functional groups present in each of the plurality of samples are quantified relative to one another from analysis of the x-ray absorption fine structure data. In 406, which can be before or after steps 401 to 405, a corrosion rate is determined for each of the plurality of samples. In 407, the corrosion rate for each of the plurality of samples is correlated with the relative amounts of each functional group identified in each of the plurality of samples to create the corrosion prediction model in the form of an equation of corrosion rate as a function of relative amounts of functional groups.

The corrosion prediction model can be used to predict a corrosion rate of a crude oil derived sample for which the corrosion rate is not known. In step 408, the crude oil derived sample is subjected to a range of x-ray energies to obtain x-ray absorption fine structure data in the form of absorbance versus x-ray energy. As in steps 402 through 405, in steps 409 through 412, functional groups present in the crude oil derived sample are identified and quantified relative to one another from analysis of the x-ray absorption fine structure data. In step 413, the corrosion prediction model is then solved for corrosion rate as a function of the relative amounts of the functional groups identified in the crude oil derived sample to obtain a prediction of the corrosion rate of the crude oil derived sample.

Figure 5:
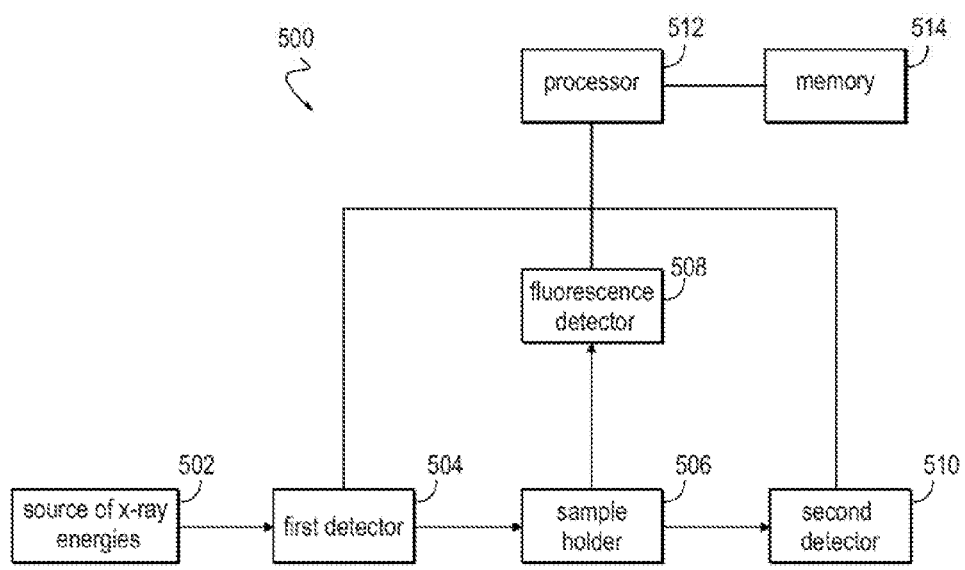
FIG. 5 is a simplified illustration of a system according to one exemplary embodiment.

FIG. 5 is a simplified illustration of a system 500 according to one exemplary embodiment. A source of a range of x-ray energies 502 directs an x-ray beam at a sample holder 506 adapted to subject a sample to the range of x-ray energies. A first detector 504 collects an initial or incoming x-ray intensity signal. A fluorescence detector 508 collects a fluorescence intensity signal from the sample. A second detector 510 optionally collects a transmitted x-ray intensity from the sample. At least one processor 512 is connected so as to receive the intensity signals from the detectors 504, 508 and 510. The at least one processor 512 can further transform the intensity signals into x-ray absorption fine structure data in the form of absorbance versus x-ray energy; compare the x-ray absorption fine structure data to a set of reference patterns for identifying and quantifying relative amounts of the functional groups present; receive and correlate corrosion rates and relative amounts of each functional group identified to create a corrosion prediction model in the form of an equation of corrosion rate as a function of relative amounts of functional groups; and solve the corrosion prediction model for corrosion rate as a function of the relative amounts of the functional groups identified to obtain a prediction of corrosion rate. An optional memory 514 is connected to the processor 512. The memory 514 can be used to store the set of reference patterns and the corrosion prediction model.

In one embodiment, the present method can be used to show that the presence of certain types of sulfur species correlate with an increase in corrosion rate, and to use the corrosion prediction model with the sulfur speciation information from XAS data as a predictive tool for sulfidation. A similar approach can be followed to identify the oxygen species in crude oils to develop a correlation for the acidic crudes that have organic acid corrosion as a significant concern.

The ability to predict how corrosive a crude oil is without having to run a corrosion test has many advantages and will be highly valuable to crude traders and processing plants. Currently, the industry standard is to use a compilation of field data showing the corrosion rate as a function of time for a set of commonly used alloys. To account for differences in sulfur content, for example, there is a correction factor that scales these rates with total sulfur content, but does not account for the different types of sulfur whose reactivity can vary by more than an order of magnitude. Incorporating the extra information XAS can provide about the relative amounts of relevant functional groups into the current models will greatly improve corrosion predictions. This can help more accurately price crude oils and may allow crude oils to be processed more safely and efficiently.

For accurate calculation of the relative amounts of each component in the XANES analysis, data must be free of distortions and uncontrolled variations coming from inconsistent sample preparation. To accomplish this, samples must be thin and homogenous and within the concentration limits relevant to each heteroatom absorption edge. This is relatively straightforward with liquids.

While reference in the above description is made to XANES, the same fitting parameters can be used with EXAFS. It is noted that this may be less preferred for a few reasons. EXAFS may have poorer signal to noise and may be prone to background artifacts at low energies, as is the case for sulfur. Furthermore, heterogeneity can cause an increased static Debye-Waller factor which damps the EXAFS at high k, which may make fitting with models problematic.

It should be noted that only the components relevant to the disclosure are shown in the figures, and that many other components normally part of an X-ray absorption spectroscopy system are not shown for simplicity.

EXAMPLES

Beamline 4.3 at the Stanford Synchrotron Radiation Lightsource (SSRL) at the SLAC National Accelerator Laboratory (Menlo Park, Calif.) was used as the source of x-ray energies. The beamline used a 20-pole, 2 Tesla wiggler source capable of an energy range of 2400 to 14000 eV. The set up included a liquid nitrogen cooled Si (111) double crystal non fixed exit slit monochrometer. The sample environment was an ambient helium atmosphere gas tight sample box for room temperature measurements with ionization chambers and a fluorescence detector. After the sample holder was loaded into the sample chamber, the chamber was purged with helium. A low flow of helium was kept on during the entire data collection scan.

The experimental set up illustrated in FIG. 3 was used. The sample holder was placed at an angle of 45° with respect to the incident incoming x-ray beam. Approximately 1 mL sample volumes were tested. The sample holders were sealed using a polytetrafluoroethylene holder with a polypropylene polymer film. Upstream of the sample holder was a ion chamber for measuring the incoming x-ray intensity ($I_o$). A fluorescence detector measured the fluorescence intensity ($I_f$). For each raw data spectrum collected, the ratio of $I_o/I_f$ was plotted versus energy (eV) and normalized by a computer processor.

Using the datfit function in the EXAFSPAK program (an operating system independent package for analysis of X-ray absorption spectroscopic data available from the SLAC National Accelerator Laboratory, Menlo Park, Calif.), each unknown raw data spectrum was matched to a set of reference standard spectra. If the number of components species within a sample is not known, a principal component analysis step can be done to estimate the number of components that should be used. As a result of the analysis of six samples, the relative amounts of the sulfur species listed in Table 1 were determined.

Figure 2:
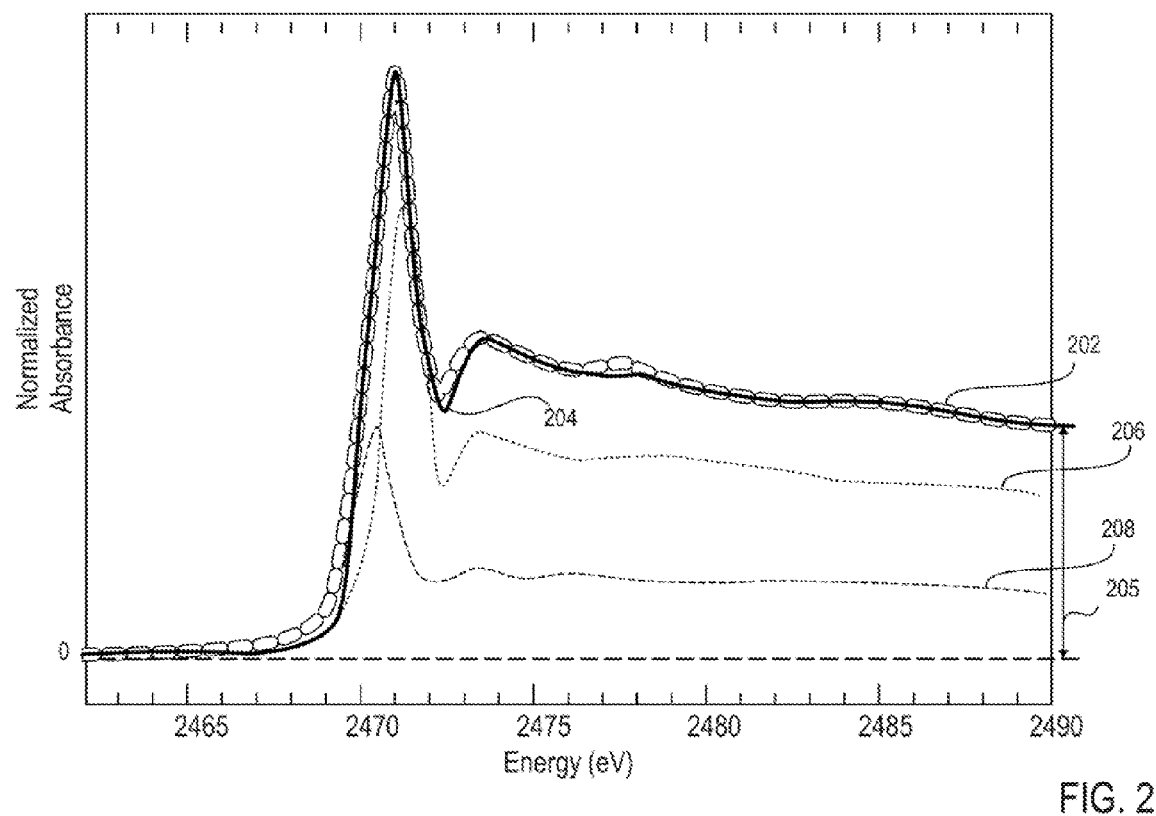
FIG. 2 is a plot of the sulfur edge of a vacuum gas oil sample known to have a notably high corrosion rate. The spectrum was fit to two components: thiophene and a sulfide.

The sulfur XANES spectrum from the VGO sample of Example 5 is shown in FIG. 2, displayed as the normalized spectrum from the VGO (202) overlaid on the linear combination of the identified components (204). Reference numeral 205 refers to the edge jump, used in the normalization of the spectrum. Analysis of the spectrum identified two major components in this particular crude oil, namely thiophene (206) and sulfide (208). This oil was known to have a higher corrosion rate than expected and had notably high sulfide content, higher than that of oils of a similar type. This demonstrates that XANES can be used to quantitatively measure the amount of each type of sulfur species in crude oil and its distillation fractions.

TABLE 1

| Example | Sample type | % Sulfate | % Sulfate ester | % Benzothiophene | % Sulfide | % Disulfide | % Thiol |
|---|---|---|---|---|---|---|---|
| 1 | Naphtha | 10.09 | 24.33 | | | 34.09 | 31.49 |
| 2 | Crude Oil | | | 75.03 | 24.97 | | |
| 3 | VGO | | | 72.78 | 27.22 | | |
| 4 | VGO | | | 76.26 | 23.74 | | |
| 5 | VGO | | | 69.04 | 30.96 | | |
| 6 | Crude Oil | | | 52.11 | 23.04 | 10.02 | 14.83 |

The crude oil sample of Example 6 was additionally tested for $H_2S$ and thiol according to ASTM D3227-04a (Standard Test Method for (Thiol Mercaptan) Sulfur in Gasoline, Kerosine, Aviation Turbine, and Distillate Fuels (Potentiometric Method)). No $H_2S$ was measured while 478 ppm of thiol was detected, in agreement with the XAS analysis.

For the purposes of this specification and appended claims, unless otherwise indicated, all numbers expressing quantities, percentages or proportions, and other numerical values used in the specification and claims are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one referent.

Unless otherwise specified, the recitation of a genus of elements, materials or other components, from which an individual component or mixture of components can be selected, is intended to include all possible sub-generic combinations of the listed components and mixtures thereof. Also, "comprise," "include" and its variants, are intended to be non-limiting, such that recitation of items in a list is not to the exclusion of other like items that may also be useful in the materials, compositions, methods and systems of this invention.

This written description uses examples to disclose the invention, including the best mode, and also to enable any person skilled in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated herein by reference.

From the above description, those skilled in the art will perceive improvements, changes in and modifications, which are intended to be covered by the appended claims.

What is claimed is:

1. A method for predicting a corrosion rate of a crude oil derived sample, comprising:
   a. creating a corrosion prediction model, including the steps of:
      i. subjecting a plurality of samples to a range of x-ray energies;
      ii. collecting transmitted x-ray intensity or fluorescence signals from the plurality of samples;
      iii. transforming the collected transmitted x-ray intensity or fluorescence signals to x-ray absorption fine structure data for each sample in the form of absorbance versus x-ray energy;
      iv. identifying functional groups present in each of the plurality of samples from the x-ray absorption fine structure data;
      v. quantifying relative amounts of the functional groups identified in each of the plurality of samples;
      vi. determining a corrosion rate for each of the plurality of samples; and
      vii. correlating the corrosion rate for each of the plurality of samples with the relative amounts of each functional group identified in each of the plurality of samples to create the corrosion prediction model in the form of an equation of corrosion rate as a function of relative amounts of functional groups;
   b. subjecting the crude oil derived sample for which a corrosion rate prediction is desired to a range of x-ray energies to obtain x-ray absorption fine structure data in the form of absorbance versus x-ray energy;
   c. identifying functional groups present in the crude oil derived sample from the x-ray absorption fine structure data;
   d. quantifying relative amounts of the functional groups identified in the crude oil derived sample; and
   e. solving the corrosion prediction model for corrosion rate as a function of the relative amounts of the functional groups identified in the crude oil derived sample to obtain a prediction of the corrosion rate of the crude oil derived sample.

2. The method of claim 1, wherein the x-ray absorption fine structure data for each sample has an edge associated with a rise in absorbance as x-ray energy increases.

3. The method of claim 2, wherein the x-ray absorption fine structure data for each sample has an edge jump and the x-ray absorption fine structure data for each sample is normalized such that the edge jump for each sample has an ordinate magnitude of 1.0.

4. The method of claim 1, wherein the plurality of samples comprise samples selected from the group consisting of crude oil samples, distilled fractions of crude oil, residual oil, samples produced from the processing or extraction of crude oil, water samples produced with crude oil and combinations thereof.

5. The method of claim 1, wherein the functional groups present in each of the plurality of samples and the functional groups present in the crude oil derived sample are identified by peak deconvolution wherein the x-ray absorption fine structure data for each sample is compared to a set of reference patterns.

6. The method of claim 1, wherein relative amounts of the functional groups present in each of the plurality of samples and the functional groups present in the crude oil derived sample are quantified using linear combination.

7. The method of claim 1, wherein the corrosion rate for each of the plurality of samples is determined by a method selected from the group consisting of use of a corrosion probe including an anode and use of at least one metal alloy weight loss coupon.

8. The method of claim 1, wherein the functional groups present in each of the plurality of samples and the functional groups present in the crude oil derived sample include an element selected from the group consisting of sulfur, oxygen, nitrogen, chlorine and combinations thereof.

9. The method of claim 1, wherein the plurality of samples includes at least 5 samples.

\* \* \* \* \*